United States Patent
Lehtomäki

(10) Patent No.: US 12,027,242 B2
(45) Date of Patent: Jul. 2, 2024

(54) CONTINUOUS USER IDENTITY VERIFICATION IN CLINICAL TRIALS VIA VOICE-BASED USER INTERFACE

(71) Applicant: SIGNANT HEALTH GLOBAL LLC, Blue Bell, PA (US)

(72) Inventor: Riku Lehtomäki, Helsinki (FI)

(73) Assignee: SIGNANT HEALTH GLOBAL LLC, Blue Bell, PA (US)

( * ) Notice: Subject to any disclaimer, the term of this patent is extended or adjusted under 35 U.S.C. 154(b) by 296 days.

(21) Appl. No.: 16/454,194

(22) Filed: Jun. 27, 2019

(65) Prior Publication Data

US 2020/0043576 A1 Feb. 6, 2020

(30) Foreign Application Priority Data

Jun. 29, 2018 (FI) .................................. 20185605

(51) Int. Cl.
*G16H 10/20* (2018.01)
*G10L 17/06* (2013.01)
(Continued)

(52) U.S. Cl.
CPC ............. *G16H 10/20* (2018.01); *G10L 17/06* (2013.01); *G10L 17/22* (2013.01); *G16H 15/00* (2018.01)

(58) Field of Classification Search
CPC ........ G16H 10/20; G16H 15/00; G16H 50/20; G16H 10/60; G16H 40/20; G10L 17/00;
(Continued)

(56) References Cited

U.S. PATENT DOCUMENTS

2007/0106510 A1 5/2007 Hsing et al.
2009/0089098 A1* 4/2009 Schoenberg ........... G16H 10/20
705/3
(Continued)

FOREIGN PATENT DOCUMENTS

WO WO-2020187300 A1 * 9/2020 ............. G10L 17/04

OTHER PUBLICATIONS

Committee on Patient Safety and Quality Improvement and Committee on Health Care for Underserved Women, Effective Patient-Physician Communication, Feb. 2014, American College of Obstetricians and Gynecologists, No. 587. (Year: 2014).*
(Continued)

*Primary Examiner* — Michael Tomaszewski
*Assistant Examiner* — Shyam M Goswami
(74) *Attorney, Agent, or Firm* — HOGAN LOVELLS US LLP

(57) ABSTRACT

The present disclosure allows continuously verifying user identity in clinical trials via a voice-based user interface. Voice input to a microphone is monitored. When an utterance in the monitored voice input is detected, voice recognition is applied to the detected utterance to determine a probability of the identity of a user uttering the detected utterance matching an identity of a previously set up clinical trial participant. When the probability satisfies a predetermined probability rule, the identity of the user is declared to be successfully verified as the previously set up clinical trial participant, and clinical trial entries are collected via a voice-based user interface while applying the voice recognition to each received clinical trial voice input.

15 Claims, 5 Drawing Sheets

(51) Int. Cl.
*G10L 17/22* (2013.01)
*G16H 15/00* (2018.01)

(58) Field of Classification Search
CPC ......... G10L 17/06; G10L 17/22; G10L 15/08;
G10L 15/26; G06Q 50/22; G06Q 50/24;
G06F 3/167; G06F 19/30; G06F 19/32;
G06F 19/34; G06F 19/36
See application file for complete search history.

(56) References Cited

U.S. PATENT DOCUMENTS

| | | | |
|---|---|---|---|
| 2009/0254351 A1* | 10/2009 | Shin ................. | G06F 3/167 |
| | | | 704/E15.001 |
| 2010/0088095 A1* | 4/2010 | John ................. | G10L 15/22 |
| | | | 704/235 |
| 2012/0035962 A1* | 2/2012 | Iliff ................. | G16H 50/20 |
| | | | 705/3 |
| 2014/0019128 A1 | 1/2014 | Riskin et al. | |
| 2016/0021105 A1* | 1/2016 | Pellom ............. | H04L 63/105 |
| | | | 726/7 |
| 2018/0130475 A1* | 5/2018 | Page ................. | G10L 25/84 |

OTHER PUBLICATIONS

Finnish Patent and Registration Office, Search Report, Application No. 20185605, dated Oct. 15, 2018, 2 pages.

* cited by examiner

CONTINUOUS USER IDENTITY VERIFICATION IN CLINICAL TRIALS VIA VOICE-BASED USER INTERFACE

BACKGROUND

Field

The present application generally relates to clinical trials. In particular, the present application relates to continuously verifying user identity in clinical trials via a voice-based user interface.

Description of the Related Art

Nowadays, clinical trials may utilize electronic or digital clinical trial diary (or patient diary) devices. Typically, an electronic clinical trial diary reminds a participant to fill in data (such as answers to validated questionnaires and symptoms occurrences, and/or other information about the participant's condition) at the right time and presents only the questions the participant should answer at that time. In addition, the electronic clinical trial diary may time stamp the recorded data and maintain an audit trail of changes to the data in order to ensure the integrity and validity of the data.

Typically, electronic clinical trial diaries use a text-based graphical user interface that requires the user to able to read and to use their hands to operate a physical or virtual keyboard. This leaves e.g. people with Parkinson's disease or eyesight issues, as well as illiterate people unable to use such a clinical trial diary.

Furthermore, if a current voice-based or voice-enabled user interface is used in a situation in which multiple persons are speaking in the same room, there is a risk that the voice-enable user interface incorrectly interprets persons other than the clinical trial participant speaking as giving commands or other input for the electronic clinical trial diary. This may result e.g. in incorrectly labeling answers provided by the other person(s) as given by the clinical trial participant.

This also applies to a situation in which electronic informed consent to a clinical trial is obtained using a current voice-enabled user interface. That is, this may result in incorrectly labeling answers (i.e. consent) provided by the other person(s) as given by the clinical trial participant. An example of a situation in which there are multiple persons in a room is when the clinical trial participant is a minor or a person requiring a legally authorized representative (LAR). For example, when the clinical trial participant is a minor whose parents are separated or divorced, a state agency acting as the guardian of the clinical trial participant and one or more lawyers may be present in the room with the clinical trial participant.

SUMMARY

An embodiment of an electronic device comprises a microphone, a speaker, at least one processor and at least one memory comprising computer program code. The at least one memory and the computer program code are configured to, with the at least one processor, cause the apparatus to at least:
monitor voice input to the microphone;
in response to detecting an utterance in the monitored voice input:
apply voice recognition to the detected utterance to determine a probability of the identity of a user uttering the detected utterance matching an identity of a previously set up clinical trial participant; and
in response to the determined probability satisfying a predetermined probability rule:
determine the identity of the user to be successfully verified as the previously set up clinical trial participant; and
collect one or more clinical trial entries via a voice-based user interface.

In an embodiment, alternatively or in addition to the above-described embodiments, the detected utterance comprises a login response uttered in response to a login request voice output.

In an embodiment, alternatively or in addition to the above-described embodiments, to collect the one or more clinical trial entries via the voice-based user interface, the at least one memory and the computer program code are configured to, with the at least one processor, cause the electronic device to:
in response to receiving a clinical trial voice input, apply speech recognition to the received clinical trial voice input to convert the received clinical trial voice input to clinical trial text input; and
save the converted clinical trial text input in a storage.

In an embodiment, alternatively or in addition to the above-described embodiments, to collect the one or more clinical trial entries via the voice-based user interface, the at least one memory and the computer program code are further configured to, with the at least one processor, cause the electronic device to:
output a clinical trial voice query.

In an embodiment, alternatively or in addition to the above-described embodiments, the received clinical trial voice input comprises at least one of: a clinical trial diary command, a clinical trial diary answer, and input related to informed consent to the clinical trial.

In an embodiment, alternatively or in addition to the above-described embodiments, to collect the one or more clinical trial entries via the voice-based user interface, the at least one memory and the computer program code are further configured to, with the at least one processor, cause the electronic device to:
apply the voice recognition to the received clinical trial voice input to determine the probability of the identity of the user uttering the received clinical trial voice input matching the identity of the previously set up clinical trial participant; and
save the determined probability with the corresponding converted clinical trial text input in the storage.

In an embodiment, alternatively or in addition to the above-described embodiments, to apply the voice recognition to the received clinical trial voice input, the at least one memory and the computer program code are further configured to, with the at least one processor, cause the electronic device to:
compare phonetical content of the received clinical trial voice input to a previously collected voice print of the previously set up clinical trial participant,
wherein the probability of the identity of the user uttering the received clinical trial voice input matching the identity of the previously set up clinical trial participant corresponds with the probability of the phonetical content of the received clinical trial voice input matching the previously collected voice print of the previously set up clinical trial participant.

In an embodiment, alternatively or in addition to the above-described embodiments, to apply the voice recognition to the detected utterance, the at least one memory and the computer program code are further configured to, with the at least one processor, cause the electronic device to:

compare phonetical content of the detected utterance to a previously collected voice print of the previously set up clinical trial participant, wherein the probability of the identity of the user uttering the detected utterance matching the identity of the previously set up clinical trial participant corresponds with the probability of the phonetical content of the detected utterance matching the previously collected voice print of the previously set up clinical trial participant.

In an embodiment, alternatively or in addition to the above-described embodiments, the at least one memory and the computer program code are further configured to, with the at least one processor, cause the electronic device to:

output a clinical trial voice query relating to a sensitive topic only when the applied voice recognition indicates that only the previously set up clinical trial participant is present.

In an embodiment, alternatively or in addition to the above-described embodiments, the at least one memory and the computer program code are further configured to, with the at least one processor, cause the electronic device to:

collect a voice sample from a user when setting the user up as a clinical trial participant; and generate the voice print for the clinical trial participant from the collected voice sample.

An embodiment of a method of continuously verifying user identity in clinical trials via a voice-based user interface comprises:

monitoring, by a processor, voice input to a microphone;

in response to detecting, by the processor, an utterance in the monitored voice input:

applying, by the processor, voice recognition to the detected utterance to determine a probability of the identity of a user uttering the detected utterance matching an identity of a previously set up clinical trial participant; and In response to the determined probability satisfying a predetermined probability rule:

determining, by the processor, the identity of the user to be successfully verified as the previously set up clinical trial participant; and collecting, by the processor, one or more clinical trial entries via a voice-based user interface.

In an embodiment, alternatively or in addition to the above-described embodiments, the detected utterance comprises a login response uttered in response to a login request voice output.

In an embodiment, alternatively or in addition to the above-described embodiments, the collecting of the one or more clinical trial entries via the voice-based user interface comprises:

in response to receiving a clinical trial voice input, applying, by the processor, speech recognition to the received clinical trial voice input to convert the received clinical trial voice input to clinical trial text input; and saving, by the processor, the converted clinical trial text input in a storage.

In an embodiment, alternatively or in addition to the above-described embodiments, the collecting of the one or more clinical trial entries via the voice-based user interface further comprises:

outputting a clinical trial voice query.

In an embodiment, alternatively or in addition to the above-described embodiments, the received clinical trial voice input comprises at least one of: a clinical trial diary command, a clinical trial diary answer, and input related to informed consent to the clinical trial.

In an embodiment, alternatively or in addition to the above-described embodiments, the collecting of the one or more clinical trial entries via the voice-based user interface further comprises:

applying, by the processor, the voice recognition to the received clinical trial voice input to determine the probability of the identity of the user uttering the received clinical trial voice input matching the identity of the previously set up clinical trial participant; and saving, by the processor, the determined probability with the corresponding converted clinical trial text input in the storage.

In an embodiment, alternatively or in addition to the above-described embodiments, the applying of the voice recognition to the received clinical trial voice input comprises:

comparing, by the processor, phonetical content of the received clinical trial voice input to a previously collected voice print of the previously set up clinical trial participant, wherein the probability of the identity of the user uttering the received clinical trial voice input matching the identity of the previously set up clinical trial participant corresponds with the probability of the phonetical content of the received clinical trial voice input matching the previously collected voice print of the previously set up clinical trial participant.

In an embodiment, alternatively or in addition to the above-described embodiments, the applying of the voice recognition to the detected utterance comprises:

comparing, by the processor, phonetical content of the detected utterance to a previously collected voice print of the previously set up clinical trial participant, wherein the probability of the identity of the user uttering the detected utterance matching the identity of the previously set up clinical trial participant corresponds with the probability of the phonetical content of the detected utterance matching the previously collected voice print of the previously set up clinical trial participant.

In an embodiment, alternatively or in addition to the above-described embodiments, the method further comprises:

outputting, by the processor, a clinical trial voice query relating to a sensitive topic only when the applied voice recognition indicates that only the previously set up clinical trial participant is present.

In an embodiment, alternatively or in addition to the above-described embodiments, the method further comprises:

collecting, by a processor, a voice sample from a user when setting the user up as a clinical trial participant; and generating, by a processor, the voice print for the clinical trial participant from the collected voice sample.

An embodiment of a computer program product comprises at least one computer-readable storage medium, the computer-readable storage medium comprising a set of instructions, which, when executed by one or more processors, cause an electronic device to at least perform:

monitoring voice input to a microphone;

in response to detecting an utterance in the monitored voice input:

applying voice recognition to the detected utterance to determine a probability of the identity of a user uttering the detected utterance matching an identity of a previously set up clinical trial participant; and in response to the determined probability satisfying a predetermined probability rule:

determining the identity of the user to be successfully verified as the previously set up clinical trial participant; and collecting one or more clinical trial entries via a voice-based user interface.

At least some of the embodiments allow a voice-based or voice-enabled user interface for clinical trials that makes it possible to continuously verifying user identity, that is, to continuously verify that the person speaking (e.g. giving answers to clinical trial diary queries) actually is the clinical trial participant rather than someone else in the room with the participant.

Accordingly, at least some of the embodiments allow using an electronic clinical trial diary with a voice-based or voice-enabled user interface. Furthermore, at least some of the embodiments allow performing an electronic informed consent process with a voice-based or voice-enabled user interface. Consequently, at least some of the embodiments allow e.g. people with Parkinson's disease or eyesight issues, as well as illiterate people to use an electronic clinical trial diary and to perform an electronic informed consent process.

At least some of the embodiments allow using an electronic clinical trial diary and performing an electronic informed consent process in a situation in which e.g. family member(s) are present in the same space than the clinical trial participant (where it is important that only the participant can utter commands to the electronic informed consent form or the electronic clinical trial diary application) since the invention allows differentiating between the clinical trial participant and anyone else due to utilizing voice recognition for each input.

At least some of the embodiments allow fulfilling the regulatory requirements related to clinical trials (such as any input must be attributable to the participant) by verifying for each participant action that it actually is by the participant rather than e.g. someone else in the same space.

Accordingly, at least some of the embodiments allow ensuring that the all the answers of an electronic clinical trial diary are given by the correct verified subject. Furthermore, at least some of the embodiments allow providing evidence of the verification afterwards. In other words, at least some of the embodiments allow audit trailing for a voice-based user interface in clinical trials.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings.

Like reference numerals are used to designate like parts in the accompanying drawings.

DETAILED DESCRIPTION

Reference will now be made in detail to embodiments of the present disclosure, examples of which are illustrated in the accompanying drawings. The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Herein, voice recognition (also called speaker recognition) refers to the identification of a person from characteristics of voices (i.e. voice biometrics). In other words, voice recognition aims to recognize who is speaking. More specifically, herein voice recognition is used to verify that a speaker is a known clinical trial participant.

Herein, speech recognition refers to the process of capturing spoken words using a microphone and converting them into a digitally stored set of words or text.

Figure 1:
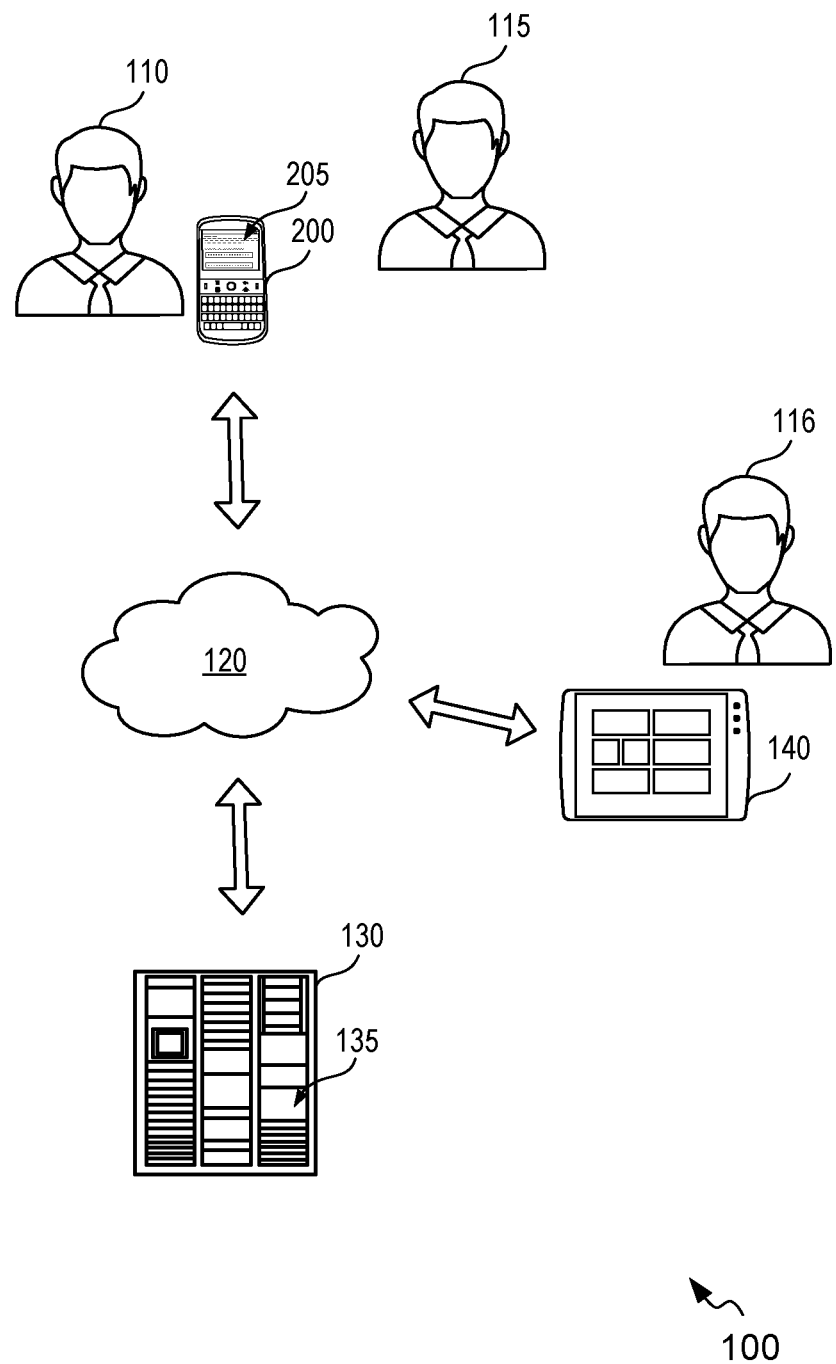
FIG. 1 illustrates an example system, where various embodiments of the present disclosure may be implemented.

FIG. 1 illustrates an example system 100, where various embodiments of the present disclosure may be implemented. An example representation of the system 100 is shown depicting a network 120 that connects entities such as a clinical trial participant 110 with an electronic device 200 used for entering clinical trial data (e.g. electronic clinical trial diary data or electronic informed consent data), a nurse 115 or the like assisting the clinical trial participant 110, a clinical trial operator 116 (e.g. a nurse or a doctor) with an electronic device 140 used to set up the clinical trial participant 110 for the clinical trial, as well as a server device 130 accessible by the electronic device 200 and the electronic device 140.

The electronic informed consent process is a part of overall clinical trial process. It is performed to fulfill regulatory requirement of obtaining informed consent. The informed consent process is a process by which a participant voluntarily confirms his or her willingness to participate in a clinical trial after having been informed of all aspects of the clinical trial that are relevant to the participant's decision to participate in the clinical trial.

An electronic clinical trial diary or electronic patient diary is an electronic tool used in clinical trials. Typically, the electronic clinical trial diary reminds a patient to fill in data (such as answers to validated questionnaires and symptoms occurrences, and/or other information about the patient's condition) at the right time and presents only the questions the patient should answer at that time. In addition, the electronic clinical trial diary may time stamp the recorded data and maintain an audit trail of changes to the data in order to ensure the integrity and validity of the data.

The network 120 may be a centralized network or it may comprise a plurality of sub-networks that may offer a direct communication between the entities or may offer indirect communication between the entities. Examples of the network 120 include wireless networks, wired networks, and combinations thereof. Some non-exhaustive examples of wireless networks may include wireless local area networks (WLANs), Bluetooth or Zigbee networks, cellular networks and the like. Some non-exhaustive examples of wired networks may include Local Area Networks (LANs), Ethernet, Fiber Optic networks and the like. An example of a combination of wired networks and wireless networks may include the Internet.

The electronic device 200 is configured to execute software 205 including a clinical trial diary application for collecting clinical trial entries and/or informed consent data via a voice-based user interface. The electronic device 200 may include e.g. a mobile phone, a smartphone, a tablet computer, a smart watch, a smart television, a wearable device, a smart device, a voice-controlled smart speaker, or any hand-held or portable device having capability to run a clinical trial diary application with a voice-based user interface.

The server device 130 may comprise a clinical trial server (or server cluster) used to e.g. manage clinical trials. Examples of the server device 130 include, but are not limited to, a desktop computer running a service, a laptop computer running a service, and/or a network server running a service. The electronic device 200 may utilize the server device 130. For example, at least some of the processes of the software product(s) 205 may be run on the server device 130 (or any other suitable server).

The electronic device 140 may be used to set up the clinical trial participant 110 for the clinical trial: The setting up may comprise e.g. collecting and storing various basic information about the participant 110, such as age, weight, other personal data, a unique identification assigned to the participant 110, and the like. Furthermore, the electronic device 140 may be used collect a voice sample from the participant 110 and to generate a voice print 135 for the participant 110 based on the collected voice sample. Typically, collecting the information and the voice sample is supervised or performed by the clinical trial operator 116, thereby allowing e.g. enhanced security since the voice sample cannot be collected from a malicious third-party. In another embodiment, collecting the information and/or the voice sample for the clinical trial set-up may be performed with the electronic device 200, e.g. under the supervision of the assisting nurse 115. Examples of the electronic device 140 include, but are not limited to, a desktop computer, a laptop computer, a smartphone, a tablet computer, a voice-controlled smart speaker, or any suitable voice-recorder device with a speaker and a microphone. The voice print 135 and/or other collected set-up information may be stored e.g. in the server device 130 from which they can be accessed by the electronic device 200 and/or the electronic device 140.

Figure 2:
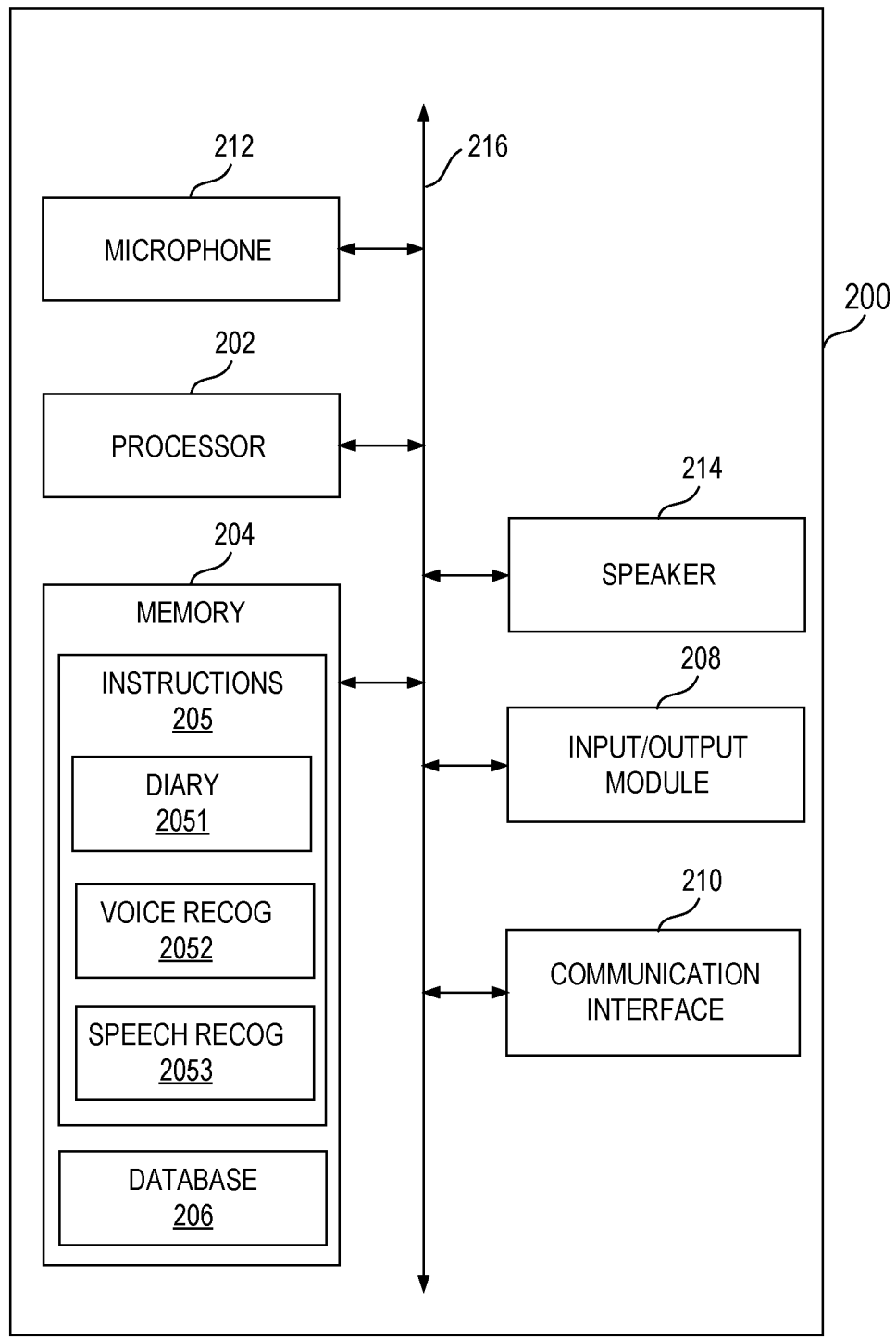
FIG. 2 is a block diagram of an electronic device configured to continuously verify user identity in clinical trials via a voice-based user interface, in accordance with an example embodiment.

FIG. 2 is a block diagram of an electronic device 200 that is configured to continuously verify user identity in clinical trials via a voice-based user interface, in accordance with an example embodiment.

The electronic device 200 comprises a microphone 212, a speaker 214, one or more processors 202, and one or more memories 204 that comprise computer program code 205.

The electronic device 200 may also include an input/output module 208, and/or a communication interface 210.

Although the electronic device 200 is depicted to include only one processor 202, the electronic device 200 may include more processors. In an embodiment, the memory 204 is capable of storing instructions 205, such an operating system and various applications, including an electronic clinical trial diary 2051, a voice recognition module 2052, and/or a speech recognition module 2053. Furthermore, the memory 204 may include a storage or database 206 that may be used e.g. to store clinical trial data input by the participant 110.

Furthermore, the processor 202 is capable of executing the stored instructions 205. In an embodiment, the processor 202 may be embodied as a multi-core processor, a single core processor, or a combination of one or more multi-core processors and one or more single core processors. For example, the processor 202 may be embodied as one or more of various processing devices, such as a coprocessor, a microprocessor, a controller, a digital signal processor (DSP), a processing circuitry with or without an accompanying DSP, or various other processing devices including integrated circuits such as, for example, an application specific integrated circuit (ASIC), a field programmable gate array (FPGA), a microcontroller unit (MCU), a hardware accelerator, a special-purpose computer chip, or the like. In an embodiment, the processor 202 may be configured to execute hard-coded functionality. In an embodiment, the processor 202 is embodied as an executor of software instructions, wherein the instructions may specifically configure the processor 202 to perform the algorithms and/or operations described herein when the instructions are executed.

The memory 204 may be embodied as one or more volatile memory devices, one or more non-volatile memory devices, and/or a combination of one or more volatile memory devices and non-volatile memory devices. For example, the memory 204 may be embodied as semiconductor memories (such as mask ROM, PROM (programmable ROM), EPROM (erasable PROM), flash ROM, RAM (random access memory), etc.).

The input/output module (hereinafter referred to as 'I/O module') 208 is configured to facilitate provisioning of an output and/or receiving an input. The I/O module 208 is configured to be in communication with the processor 202 and the memory 204. Examples of the I/O module 208 include, but are not limited to, an input interface and/or an output interface. Examples of the input interface may include, but are not limited to, a keypad, a touch screen, soft keys, and the like. Examples of the output interface may include, but are not limited to, a display such as a light emitting diode display, a thin-film transistor (TFT) display, a liquid crystal display, an active-matrix organic light-emitting diode (AMOLED) display, and the like. In an example embodiment, the processor 202 may include I/O circuitry configured to control at least some functions of one or more elements of the I/O module 208, such as, for example, a display, and/or the like, as well as the speaker 214 and/or the microphone 212. The processor 202 and/or the I/O circuitry may be configured to control one or more functions of the one or more elements of the I/O module 208 through computer program instructions, for example, software and/or firmware, stored on a memory, for example, the memory 204, and/or the like, accessible to the processor 202.

In an embodiment, the I/O module 208 may be configured to provide a user interface (UI) configured to provide options or any other display to a user of the electronic device 200. In addition, the I/O module 208 may be integrated with mechanisms configured to receive inputs from the user of the electronic device 200.

The communication interface 210 may enable the electronic device 200 to communicate with other devices. In an embodiment, various components of the electronic device 200, such as the processor 202, the memory 204, the I/O module 208 and the communication interface 210 are configured to communicate with each other via or through a centralized circuit 216. The centralized circuit 216 may be various devices configured to, among other things, provide or enable communication between the components 202-214 of the electronic device 200. In certain embodiments, the centralized circuit 216 may be a central printed circuit board (PCB) such as a motherboard, a main board, an electronic device board, or a logic board. The centralized circuit 216 may also, or alternatively, include other printed circuit assemblies (PCAs) or communication channel media.

The electronic device 200 as illustrated and hereinafter described is merely illustrative of an apparatus that could benefit from embodiments of the invention and, therefore, should not be taken to limit the scope of the invention. It is noted that the electronic device 200 may include fewer or more components than those depicted in FIG. 2.

The one or more memories 204 and the computer program code 205 are configured to, with the one or more processors 202, cause the electronic device 200 to monitor (or listen to) voice input to the microphone 212.

When an utterance (e.g. start word(s) or wake word(s), such as "Wake up Saga" or the like, a login response uttered by a user in response to a login request voice output e.g. via the speaker 214, and/or any suitable utterance to which voice recognition can be applied) is detected in the monitored voice input, the one or more memories 204 and the computer program code 205 are further configured to, with the one or more processors 202, cause the electronic device 200 to apply voice recognition to the detected utterance to determine a probability of the identity of a user uttering the detected utterance matching an identity of a previously set up clinical trial participant 110.

When the login request (and the login response) is utilized, it can be any suitable utterance. An example of the spoken login request includes "Please state your subject code". An example of a corresponding spoken login response may include "003" or the like. Other examples of the spoken login request include "What is your favorite color" and "What is your name". The login request may be e.g. a simple question. In an embodiment, the word content of the login response does not matter (i.e. there is no single "correct" answer to the login request). Instead, it is the result of the applied voice recognition that matters. Furthermore, the login response may be common knowledge (for example, known by other people present with the participant 110, such as the nurse 115). Again, this is of no consequence in regards to identity verification since it is the result of the applied voice recognition that matters rather than the word(s) themselves spoken by the participant 110 as the login response.

To apply the voice recognition to the detected utterance, the at least one memory 204 and the computer program code 205 may be further configured to, with the at least one processor 202, cause the electronic device 200 to compare phonetical content of the detected utterance to the previously collected voice print 135 of the previously set up clinical trial participant 110. Here, the probability of the identity of the user uttering the detected utterance matching the identity of the previously set up clinical trial participant 110 corresponds with the probability of the phonetical content of the detected utterance matching the previously collected voice print 135 of the previously set up clinical trial participant 110. The voice recognition functionality may be provided e.g. by the voice recognition module 2052.

When the determined probability (or confidence value) satisfies a predetermined probability rule (e.g. exceeds or falls below a predetermined probability threshold (e.g. 95%), or falls within or outside a predetermined probability range), the one or more memories 204 and the computer program code 205 are further configured to, with the one or more processors 202, cause the electronic device 200 to determine that the identity of the user has been successfully verified as the previously set up clinical trial participant 110, and to collect one or more clinical trial entries via a voice-based user interface To collect the one or more clinical trial entries via the voice-based user interface, the at least one memory 204 and the computer program code 205 may be configured to, with the at least one processor 202, cause the electronic device 200 to output a clinical trial voice query, e.g. via the speaker 214. The clinical trial entry collection functionality may be provided e.g. by the electronic clinical trial diary 2051.

An example of the spoken clinical trial voice query includes a main menu type query, such as "What would you like to do?", or "You haven't filled in your daily diary, would you like to fill it now?"

In an embodiment, a clinical trial voice query that relates to a sensitive or private topic may be output only when the applied voice recognition indicates that only the previously set up clinical trial participant is present. In other words, the voice recognition data may be used to create conditional branching inside the clinical trial diary logic to protect sensitive parts of the clinical trial diary (for example matters that are sensitive to the participant and should not be revealed under any circumstances even to caregivers or the like). For example, a questionnaire related to sexual health may be presented only if the participant uttering the commands has been verified with high enough confidence on all commands (i.e. it can be assumed that the participant is alone answering the questions). Otherwise, the sexual health diary portion may be skipped silently.

When a clinical trial voice input is received via the microphone 212 in response to the output clinical trial query, the at least one memory 204 and the computer program code 205 may be configured to, with the at least one processor 202, cause the electronic device 200 to apply speech recognition to the received clinical trial voice input in order to convert the received clinical trial voice input to clinical trial text input, and to save the converted clinical trial text input in the storage 206. The received clinical trial voice input may comprise e.g. a clinical trial diary command (e.g. "next"), a clinical trial diary answer, and/or input related to informed consent to the clinical trial. The speech recognition functionality may be provided e.g. by the speech recognition module 2053.

In other words, the commands to the clinical trial diary and/or answers to questions may be recorded by the microphone 212 and converted to text and saved. The applied speech recognition may also recognize e.g. the end of an uttered command/answer in order to be able to divide the text strings according to speech sections.

The commands to the clinical trial diary and/or answers to questions may include a phrase or the like that indicates the end of the clinical trial diary session, such as "Are you done?". In addition/alternatively, a time-out functionality may be utilized to indicate the end of the clinical trial diary session.

Additionally, to collect the one or more clinical trial entries via the voice-based user interface, the at least one memory 204 and the computer program code 205 may be configured to, with the at least one processor 202, cause the electronic device 200 to apply the voice recognition to the received clinical trial voice input to determine the probability of the identity of the user uttering the received clinical trial voice input matching the identity of the previously set up clinical trial participant 110, and to save the determined probability with the corresponding converted clinical trial text input in the storage 206. The voice recognition functionality may be provided e.g. by the voice recognition module 2052.

In other words, in addition to the text input/command/answer saved to the storage 206, each input/command/answer may be appended with the probability of the person giving the input/command/answer being the verified participant. The probability may e.g. need to exceed a predetermined probability (or confidence) threshold (e.g. 95%) to be deemed acceptable. Alternatively, when multiple persons are present, the probabilities of all but one person not exceeding the predetermined probability threshold may be used to deduce that the remaining one person is the verified participant. An example includes:

Query: "How do you feel to day (Excellent, good, not so good, bad, terrible)?"
Response: "Excellent"
Saved entry: "John Doe, with 97% confidence" (in addition to the query or query identification and the uttered response).

To apply the voice recognition to the received clinical trial voice input, the at least one memory 204 and the computer program code 205 may be further configured to, with the at least one processor 202, cause the electronic device 200 to compare phonetical content of the received clinical trial voice input to the previously collected voice print 135 of the previously set up clinical trial participant 110. Here, the probability of the identity of the user uttering the received clinical trial voice input matching the identity of the previously set up clinical trial participant 110 corresponds with the probability of the phonetical content of the received clinical trial voice input matching the previously collected voice print of the previously set up clinical trial participant 110.

As discussed in connection with FIG. 1, the at least one memory 204 and the computer program code 205 may be further configured to, with the at least one processor 202, cause the electronic device 200 to collect the voice sample from the user when setting the user up as the clinical trial participant 110, and to generate the voice print (or voice template or voice model) 135 for the clinical trial participant 110 from the collected voice sample. Techniques used to provide a voice print may include e.g. frequency estimation, hidden Markov models, Gaussian mixture models, pattern matching algorithms, neural networks, matrix representation, vector quantization, decision trees, cohort models, and/or world models.

An example of signing a consent form in the electronic informed consent process in accordance with an example embodiment may include:

When the participant progresses to the signing phase, the voice UI says: "Please say when you're ready to give a signature"

Participant: "I'm ready" (verified)
Voice UI: "Please feel free to sign now, and when finished, say 'I'm ready'"
(Participant signs by hand)
Participant: "I'm ready" (verified)

An example of filling the electronic clinical trial diary in accordance with an example embodiment may include:

Voice UI: "Would you like to start filling in your diary?"
Participant: "Yes" (verified)
Voice UI: "On a scale from 1 to 5, how would you describe your pain?"
Participant: "Two" (verified)
...
Voice UI: "Thank you for filling in your diary. Are you ready or do you want to change your answers?"
Participant: "Yes" (verified)
(Diary closes)

In an embodiment, the electronic device 200 may effectively act as a voice recorder to record an informed consent session, such that a clinical trial staff member (or the like) presses a button or otherwise triggers recording of an informed consent session, thus not requiring a login request/response or start utterance. In this embodiment, the electronic device 200 may be constantly recording while the clinical trial staff member is providing information to the clinical trial participant and the clinical trial participant is asking questions. Here, the data can be stored by tagging each data entry with the speaker probability. No login is request/response required when the data is associated with e.g. consent identification and/or participant identification before or when the informed consent session starts. In an embodiment, the recording or parts of it may be saved permanently or temporarily in a cloud.

Furthermore, if there are more people present, the speakers may be tagged e.g. as "Person A", "Person B", etc., and they may be declared by the clinical trial staff member at the start of the session with a statement, such as "The person who just spoke is John Doe" or the clinical trial staff member may request each person in the room to "please state your full name" thus allowing a voice print to be generated for each person present.

Figure 3A:
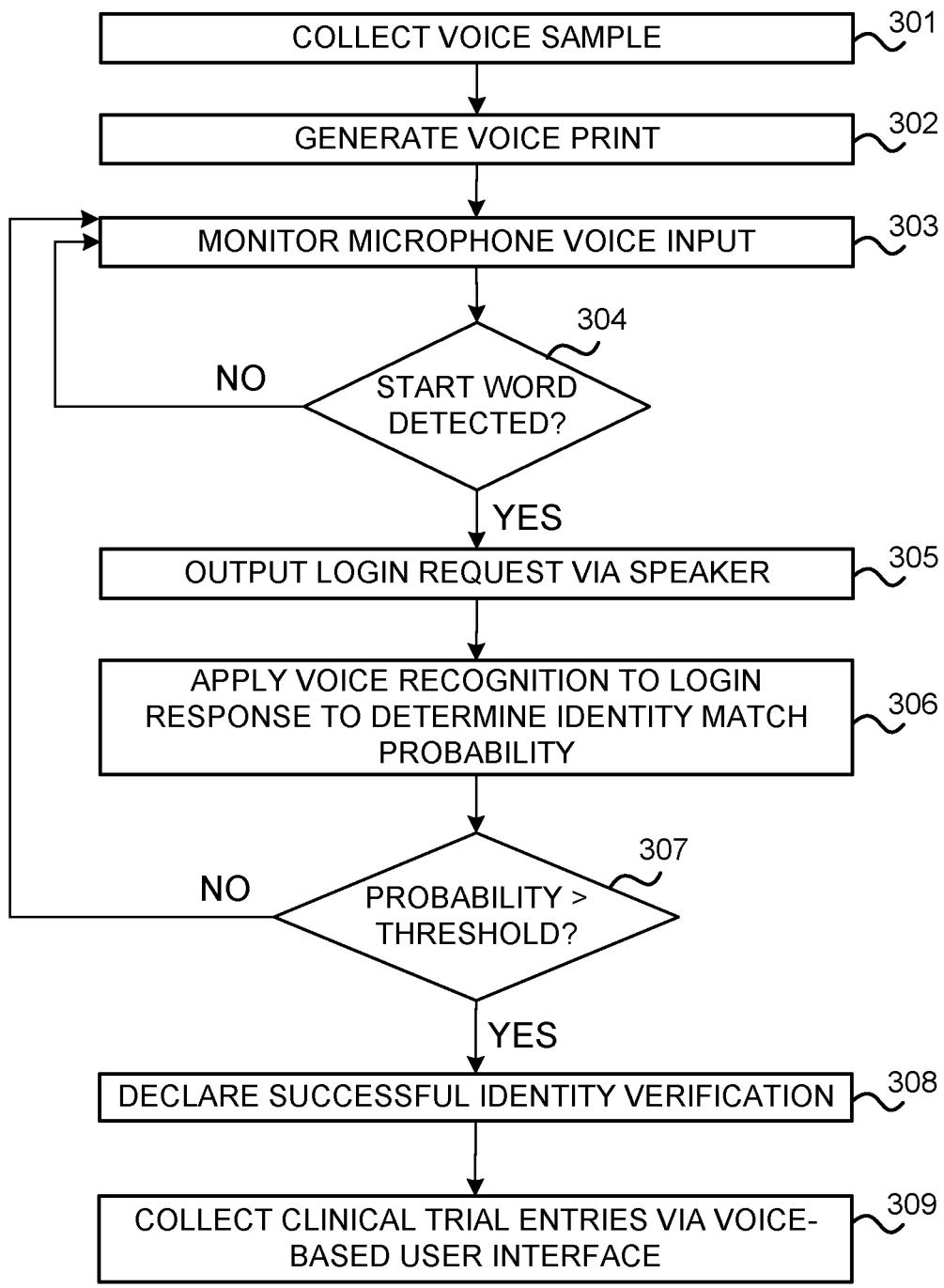
FIG. 3A illustrates an example flow diagram of a method of continuously verifying user identity in clinical trials via a voice-based user interface, in accordance with an example embodiment.

FIG. 3A illustrates an example flow diagram of a method 300 of continuously verifying user identity in clinical trials via a voice-based user interface, in accordance with an example embodiment.

At optional operation 301, a voice sample is collected from a user by a processor when setting the user up as a clinical trial participant.

At optional operation 302, a voice print for a clinical trial participant (i.e. the user) is generated by the processor from the collected voice sample.

At operation 303, voice input to a microphone is monitored by the processor.

At optional operation 304, if a start utterance (such as a start word or the like) is detected by the processor in the monitored voice input, the method proceeds to operation 305. Otherwise, the method may return to operation 303.

At optional operation 305, a login request is output, e.g. via a speaker.

At operation 306, voice recognition is applied by the processor to a detected utterance (such as a subsequent login response to the login request) to determine a probability of the identity of a user uttering the detected utterance (e.g. the login response) matching an identity of a previously set up clinical trial participant. In an example, the applying of the voice recognition to the detected utterance (e.g. the login voice response) may comprise the processor comparing phonetical content of the detected utterance (e.g. the login voice response) to a previously collected voice print of the previously set up clinical trial participant. In this case, the probability of the identity of the user uttering the detected utterance (e.g. the login voice response) matching the identity of the previously set up clinical trial participant corresponds with the probability of the phonetical content of the detected utterance (e.g. the login voice response) matching the previously collected voice print of the previously set up clinical trial participant.

At operation 307, if the determined probability satisfies a predetermined probability rule (e.g. exceeds or falls below a predetermined threshold, or falls within or outside a predetermined probability range), the method proceeds to operation 308. Otherwise, the method may return to operation 303, or alternatively the method may exit (not shown in FIG. 3A).

At operation 308, the identity of the user is determined by the processor to be successfully verified as the previously set up clinical trial participant.

At operation 309, one or more clinical trial entries are collected by the processor via a voice-based user interface. After collecting all the clinical trial entries, the method may exit (not shown in FIG. 3A).

Figure 4:
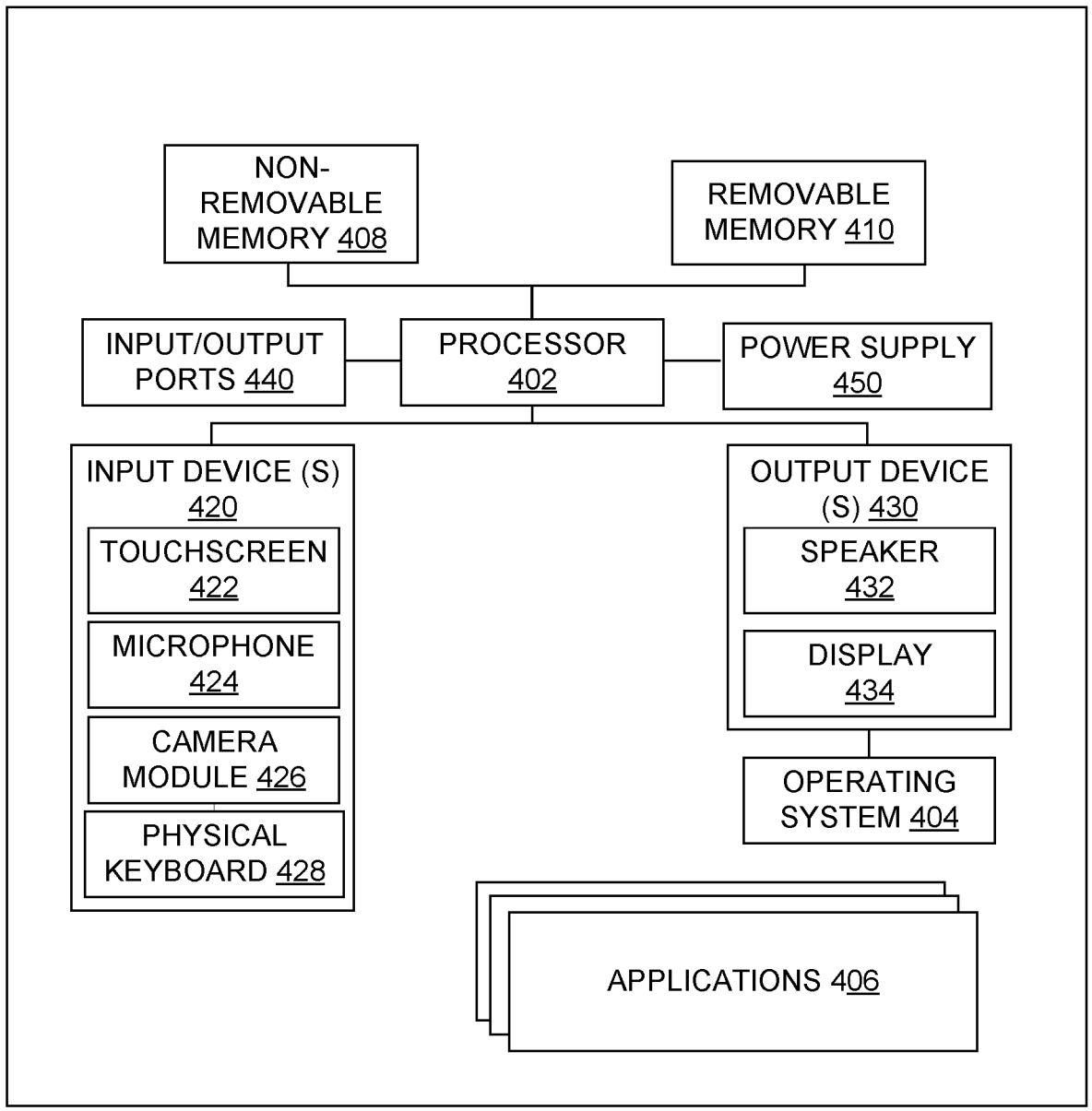
FIG. 4 illustrates an example of an apparatus capable of implementing example embodiments described herein.

The method 300 may be performed by the electronic device 200 of FIG. 2 or the apparatus 400 of FIG. 4. Further features of the method 300 directly result from the functionalities and parameters of the electronic device 200 and thus are not repeated here. The method 300 can be performed by computer program(s).

Figure 3B:
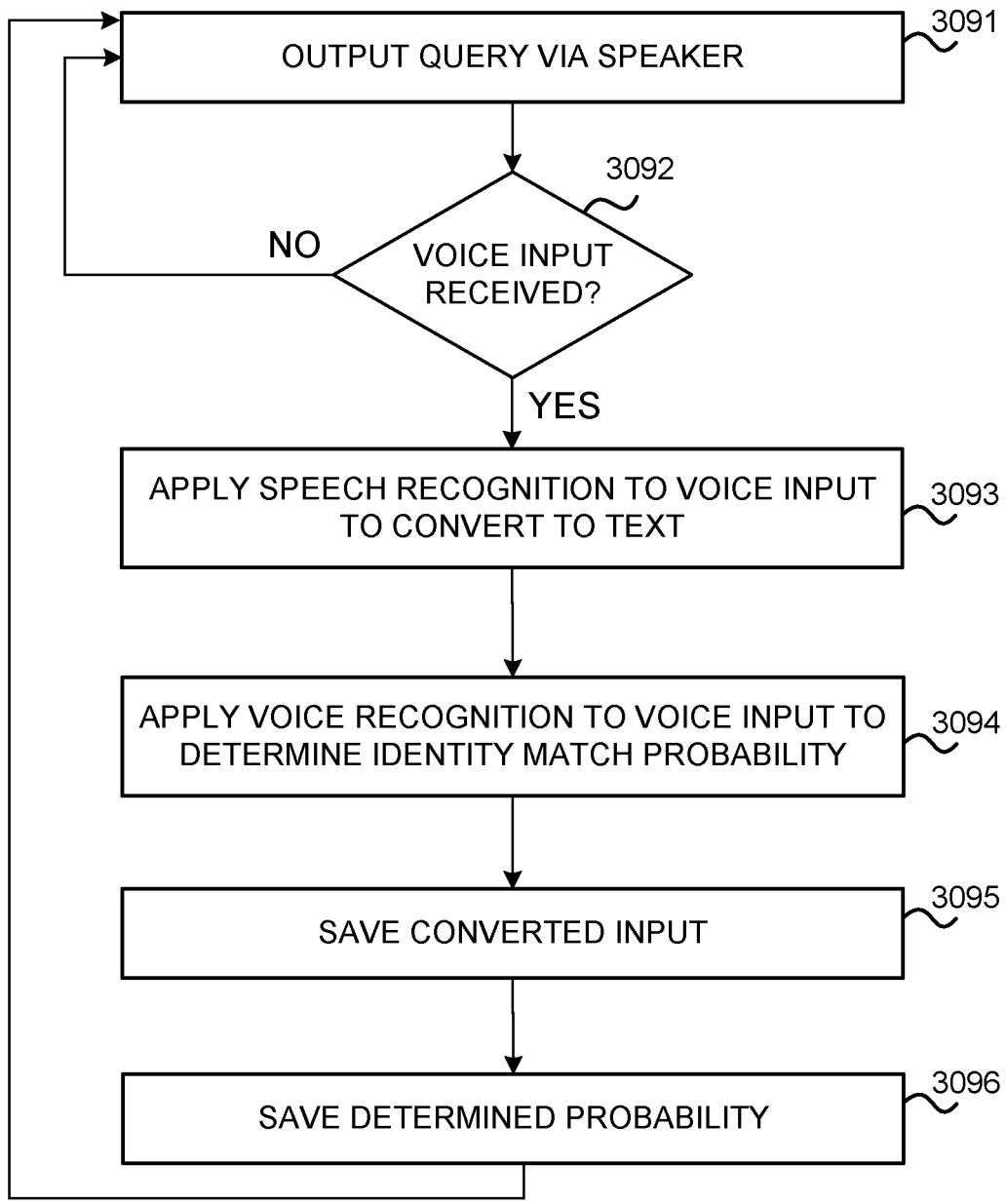
FIG. 3B illustrates an example flow diagram of implementing the collecting of the clinical trial entries of FIG. 3A via the voice-based user interface, in accordance with an example embodiment.

FIG. 3B illustrates an example flow diagram of a method 350 of implementing the operation 309 of FIG. 3A, in accordance with an example embodiment.

At operation 3091, a clinical trial voice query is output, e.g. via the speaker. The query may relate e.g. to a clinical trial diary entry, or to informed consent to the clinical trial. In an embodiment, a clinical trial voice query that relates to a sensitive or private topic may be output only when the previously applied (at operation 306 or at previous instances of operation 3094 during a same session) voice recognition indicates that only the previously set up clinical trial participant is present.

At operation 3092, if a clinical trial voice input is received via the microphone, the method proceeds to operation 3093. Otherwise, the method may e.g. return to operation 3091. The received clinical trial voice input may comprise e.g. a clinical trial diary command for controlling the clinical trial diary, a clinical trial diary answer, and/or input related to informed consent to the clinical trial.

At operation 3093, speech recognition is applied by the processor to the received clinical trial voice input to convert the received clinical trial voice input to clinical trial text input.

At operation 3094, the voice recognition is applied by the processor to the received clinical trial voice input to determine the probability of the identity of the user uttering the received clinical trial voice input matching the identity of the previously set up clinical trial participant. In an example, the applying of the voice recognition to the received clinical trial voice input may comprise the processor comparing phonetical content of the received clinical trial voice input to a previously collected voice print of the previously set up clinical trial participant. In this case, the probability of the identity of the user uttering the received clinical trial voice input matching the identity of the previously set up clinical trial participant corresponds with the probability of the phonetical content of the received clinical trial voice input matching the previously collected voice print of the previously set up clinical trial participant.

At operation 3095, the converted clinical trial text input is saved by the processor in a storage.

At operation 3096, the determined probability is saved by the processor with the corresponding converted clinical trial text input in the storage.

Next, the method may e.g. return to operation 3091 in order to proceed to a next query. Alternatively, the method may exit (not shown in FIG. 3B).

The method 350 may be performed by the electronic device 200 of FIG. 2 or the apparatus 400 of FIG. 4. Further features of the method 350 directly result from the functionalities and parameters of the electronic device 200 and thus are not repeated here. The method 350 can be performed by computer program(s).

FIG. 4 further illustrates an example of an apparatus 400 capable of implementing example embodiments of the electronic device 200 described herein. It should be understood that the apparatus 400 as illustrated and hereinafter described is merely illustrative of one type of electronic apparatus or device and should not be taken to limit the scope of the embodiments. As such, it should be appreciated that at least some of the components described below in connection with the apparatus 400 may be optional and thus in an example embodiment may include more, less or different components than those described in connection with the example embodiment of FIG. 4. As such, among other examples, the apparatus 400 could be any suitable computer device capable of speech and voice recognition, such as smart phone or a tablet computer that is capable of speech and voice recognition, or the like.

The illustrated apparatus 400 includes a controller or a processor 402 (i.e. a signal processor, microprocessor, ASIC, or other control and processing logic circuitry) for performing such tasks as signal coding, data processing, input/output processing, power control, and/or other functions. An operating system 404 controls the allocation and usage of the components of the apparatus 400 and support for one or more application programs 406. The application programs 406 can include applications related to clinical trial diaries, or any other applications.

The illustrated apparatus 400 includes one or more memory components, for example, a non-removable memory 408 and/or removable memory 410. The non-removable memory 408 may include RAM, ROM, flash memory, a hard disk, or other well-known memory storage technologies. The removable memory 410 may include flash memory (such as one or more removable flash drives) or smart cards. The one or more memory components may be used for storing data and/or code for running the operating system 404 and the applications 406. Example of data may include text, images, sound files, image data, video data, or other data sets to be sent to and/or received from one or more network servers or other devices via one or more wired or wireless networks.

The apparatus 400 can support one or more input devices 420 and one or more output devices 430. Examples of the input devices 420 may include, but are not limited to, a touchscreen 422 (i.e., capable of capturing finger tap inputs, finger gesture inputs, multi-finger tap inputs, multi-finger gesture inputs, or keystroke inputs from a virtual keyboard or keypad), a microphone 424 (i.e., capable of capturing voice input), a camera module 426 (i.e., capable of capturing still picture images and/or video images) and a physical keyboard 428. Examples of the output devices 430 may include, but are not limited to a speaker 432 and a display 434. Other possible output devices (not shown) can include piezoelectric or other haptic output devices. Some devices can serve more than one input/output function. For example, the touchscreen 422 and the display 434 can be combined into a single input/output device.

The apparatus 400 can further include one or more input/output ports 440, and a power supply 450. The illustrated components are not required or all-inclusive, as any of the components shown can be deleted and other components can be added.

The exemplary embodiments can include, for example, any suitable computer devices and the like, capable of performing the processes of the exemplary embodiments. The devices and subsystems of the exemplary embodiments can communicate with each other using any suitable protocol and can be implemented using one or more programmed computer systems or devices.

One or more interface mechanisms can be used with the exemplary embodiments, including, for example, Internet access, telecommunications in any suitable form (e.g., voice, modem, and the like), wireless communications media, and the like. For example, employed communications networks or links can include one or more satellite communications networks, wireless communications networks, cellular communications networks, 3G communications networks, 4G communications networks, Public Switched Telephone Network (PSTNs), Packet Data Networks (PDNs), the Internet, intranets, a combination thereof, and the like.

It is to be understood that the exemplary embodiments are for exemplary purposes, as many variations of the specific hardware used to implement the exemplary embodiments are possible, as will be appreciated by those skilled in the hardware and/or software art(s). For example, the functionality of one or more of the components of the exemplary embodiments can be implemented via one or more hardware and/or software devices.

The exemplary embodiments can store information relating to various processes described herein. This information can be stored in one or more memories, such as a hard disk, optical disk, magneto-optical disk, RAM, and the like. One or more databases can store the information used to implement the exemplary embodiments of the present inventions. The databases can be organized using data structures (e.g., records, tables, arrays, fields, graphs, trees, lists, and the like) included in one or more memories or storage devices listed herein. The processes described with respect to the exemplary embodiments can include appropriate data structures for storing data collected and/or generated by the processes of the devices and subsystems of the exemplary embodiments in one or more databases.

All or a portion of the exemplary embodiments can be conveniently implemented using one or more general purpose processors, microprocessors, digital signal processors, micro-controllers, and the like, programmed according to the teachings of the exemplary embodiments of the present inventions, as will be appreciated by those skilled in the computer and/or software art(s). Appropriate software can be readily prepared by programmers of ordinary skill based on the teachings of the exemplary embodiments, as will be appreciated by those skilled in the software art. In addition, the exemplary embodiments can be implemented by the preparation of application-specific integrated circuits or by interconnecting an appropriate network of conventional component circuits, as will be appreciated by those skilled in the electrical art(s). Thus, the exemplary embodiments are not limited to any specific combination of hardware and/or software.

Stored on any one or on a combination of computer readable media, the exemplary embodiments of the present inventions can include software for controlling the components of the exemplary embodiments, for driving the components of the exemplary embodiments, for enabling the components of the exemplary embodiments to interact with a human user, and the like. Such software can include, but is not limited to, device drivers, firmware, operating systems, development tools, applications software, and the like. Such computer readable media further can include the computer program product of an embodiment of the present inventions for performing all or a portion (if processing is distributed) of the processing performed in implementing the inventions. Computer code devices of the exemplary embodiments of the present inventions can include any suitable interpretable or executable code mechanism, including but not limited to scripts, interpretable programs, dynamic link libraries (DLLs), Java classes and applets, complete executable programs, Common Passenger Request Broker Architecture (CORBA) passengers, and the like. Moreover, parts of the processing of the exemplary embodiments of the present inventions can be distributed for better performance, reliability, cost, and the like.

As stated above, the components of the exemplary embodiments can include computer readable medium or memories for holding instructions programmed according to the teachings of the present inventions and for holding data structures, tables, records, and/or other data described herein. Computer readable medium can include any suitable medium that participates in providing instructions to a processor for execution. Such a medium can take many forms, including but not limited to, non-volatile media, volatile media, and the like. Non-volatile media can include, for example, optical or magnetic disks, magneto-optical disks, and the like. Volatile media can include dynamic memories, and the like. Common forms of computer-readable media can include, for example, a floppy disk, a flexible disk, hard disk, or any other suitable medium from which a computer can read.

While the present disclosure has been de-scribed in connection with a number of exemplary embodiments, and implementations, the present disclosure is not so limited, but rather covers various modifications, and equivalent arrangements, which fall within the purview of prospective claims.

The invention claimed is:

1. An electronic device, comprising:
    a microphone;
    a speaker;
    at least one processor;
    a storage; and
    at least one memory comprising computer program code, wherein the at least one memory and the computer program code are configured to, with the at least one processor, cause the electronic device to at least:
        monitor voice input to the microphone, in a clinical trial session or informed consent session with at least two users present;
        in response to detecting an utterance in the monitored voice input:
            apply voice recognition, by the processor, which compares a phonetical content of the detected utterance to a previously collected voice print of a previously set up clinical trial participant, to determine a probability of an identity of a first user from the at least two users, uttering the detected utterance matching an identity of the previously set up clinical trial participant; and in response to the determined probability satisfying a predetermined probability rule:
  determine the identity of the first user, to be successfully verified as the previously set up clinical trial participant;
collect one or more clinical trial entries via a voice-based user interface;
in response to receiving a clinical trial voice input, apply speech recognition to the received clinical trial voice input to convert the received clinical trial voice input to clinical trial text input;
apply the voice recognition to the received clinical trial voice input to determine a probability of the identity of the first user uttering the received clinical trial voice input matching the identity of the previously set up clinical trial participant; and
save the determined probability of the identity of the first user uttering the received clinical trial voice input matching the identity of the previously set up clinical trial participant with the corresponding converted clinical trial text input in the storage;
wherein the voice-based user interface outputs a clinical trial voice query relating to a topic after the applied voice recognition indicates that only the first user from the at least two users is present, based at least in part on a verification corresponding to the first user using at least the received clinical trial voice input appended with the determined probability of the identity of the user uttering the received clinical trial voice input matching the identity of the previously set up clinical trial participant, the determined probability appended with at least the received clinical trial voice input exceeding a threshold, with the verification of the first user made subsequent to the verification of the identity of the first user.

2. The electronic device according to claim 1, wherein the detected utterance comprises a login response uttered in response to a login request voice output.

3. The electronic device according to claim 1, further comprising, the at least one memory and the computer program code are configured to, with the at least one processor, cause the electronic device to:
save the converted clinical trial text input in the storage.

4. The electronic device according to claim 3, wherein the received clinical trial voice input comprises at least one of: a clinical trial diary command, a clinical trial diary answer, and input related to informed consent to the clinical trial.

5. The electronic device according to claim 3, wherein, to apply the voice recognition to the received clinical trial voice input, the at least one memory and the computer program code are further configured to, with the at least one processor, cause the electronic device to:
determine that the probability of the identity of the user uttering the received clinical trial voice input matching the identity of the previously set up clinical trial participant corresponds with the probability of the phonetical content of the received clinical trial voice input matching the previously collected voice print of the previously set up clinical trial participant.

6. The electronic device according to claim 1, wherein, to apply the voice recognition to the detected utterance, the at least one memory and the computer program code are further configured to, with the at least one processor, cause the electronic device to:
determine that the probability of the identity of the user uttering the detected utterance matching the identity of the previously set up clinical trial participant corresponds with the probability of the phonetical content of the detected utterance matching the previously collected voice print of the previously set up clinical trial participant.

7. The electronic device according to claim 5, wherein, the at least one memory and the computer program code are further configured to, with the at least one processor, cause the electronic device to:
collect a voice sample from a user when setting the user up as a clinical trial participant; and
generate the voice print for the clinical trial participant from the collected voice sample.

8. A method of continuously verifying user identity in a clinical trial session or informed consent session via a voice-based user interface, comprising:
monitoring, by a processor, voice input to a microphone in the clinical trial session or informed consent session with at least two users present;
in response to detecting, by the processor, an utterance in the monitored voice input:
  applying, by the processor, voice recognition, by comparing a phonetical content of the detected utterance to a previously collected voice print of a previously set up clinical trial participant to determine a probability of an identity of a first user from the at least two users, uttering the detected utterance matching an identity of a previously set up clinical trial participant; and
in response to the determined probability satisfying a predetermined probability rule:
  determining, by the processor, the identity of the first user, to be successfully verified as the previously set up clinical trial participant;
collecting, by the processor, one or more clinical trial entries via a voice-based user interface;
in response to receiving a clinical trial voice input, apply speech recognition to the received clinical trial voice input to convert the received clinical trial voice input to clinical trial text input;
applying, by the processor, the voice recognition to the received clinical trial voice input to determine the probability of the identity of the first user uttering the received clinical trial voice input matching the identity of the previously set up clinical trial participant; and
saving, by the processor, the determined probability of the identity of the first user uttering the received clinical trial voice input matching the identity of the previously set up clinical trial participant with the corresponding converted clinical trial text input in a storage;
wherein the voice-based user interface outputs a clinical trial voice query relating to a topic after the applied voice recognition indicates that only the first user from the at least two users is present, based at least in part on a verification corresponding to the first user using at least the received clinical trial voice input appended with the determined probability of the identity of the user uttering the received clinical trial voice input matching the identity of the previously set up clinical trial participant, the determined probability appended with at least the received clinical trial voice input exceeding a threshold, with the verification of the first user made subsequent to the verification of the identity of the first user.

9. The method according to claim 8, wherein the detected utterance comprises a login response uttered in response to a login request voice output.

10. The method according to claim 8, wherein the collecting of the one or more clinical trial entries via the voice-based user interface comprises: in response to receiving a clinical trial voice input, applying, by the processor, speech recognition to the received clinical trial voice input to convert the received clinical trial voice input to clinical trial text input; and saving, by the processor, the converted clinical trial text input in the storage.

11. The method according to claim 10, wherein the received clinical trial voice input comprises at least one of: a clinical trial diary command, a clinical trial diary answer, and input related to informed consent to the clinical trial.

12. The method according to claim 10, wherein the applying of the voice recognition to the received clinical trial voice input comprises:
  determining that the probability of the identity of the user uttering the received clinical trial voice input matching the identity of the previously set up clinical trial participant corresponds with the probability of the phonetical content of the received clinical trial voice input matching the previously collected voice print of the previously set up clinical trial participant.

13. The method according to claim 8, wherein the applying of the voice recognition to the detected utterance comprises:
  determining that the probability of the identity of the user uttering the detected utterance matching the identity of the previously set up clinical trial participant corresponds with the probability of the phonetical content of the detected utterance matching the previously collected voice print of the previously set up clinical trial participant.

14. The method according to claim 12, further comprising:
  collecting, by the processor, a voice sample from a user when setting the user up as a clinical trial participant; and
    generating, by the processor, the voice print for the clinical trial participant from the collected voice sample.

15. A computer program product comprising at least one non-transitory computer-readable storage medium, wherein the computer-readable storage medium comprises a set of instructions, which, when executed by one or more processors, cause an electronic device to at least perform:
  monitoring voice input to a microphone in a clinical trial session or informed consent session with at least two users present;
  in response to detecting an utterance in the monitored voice input:
    applying voice recognition, by the processor, which compares a phonetical content of the detected utterance to a previously collected voice print of a previously set up clinical trial participant, to determine a probability of an identity of a first user from the at least two users, uttering the detected utterance matching an identity of a previously set up clinical trial participant; and
  in response to the determined probability satisfying a predetermined probability rule:
    determining the identity of the first user, to be successfully verified as the previously set up clinical trial participant;
  collecting one or more clinical trial entries via a voice-based user interface;
  in response to receiving a clinical trial voice input, apply speech recognition to the received clinical trial voice input to convert the received clinical trial voice input to clinical trial text input;
  applying, by the processor, the voice recognition to the received clinical trial voice input to determine the probability of the identity of the first user uttering the received clinical trial voice input matching the identity of the previously set up clinical trial participant; and
  saving, by the processor, the determined probability with the corresponding converted clinical trial text input in a storage;
  wherein the voice-based user interface outputs a clinical trial voice query relating to a topic after the applied voice recognition indicates that only the first user from the at least two users is present, based at least in part on a verification corresponding to the first user using at least the received clinical trial voice input appended with the determined probability of the identity of the user uttering the received clinical trial voice input matching the identity of the previously set up clinical trial participant, the determined probability appended with at least the received clinical trial voice input exceeding a threshold, with the verification of the first user made subsequent to the verification of the identity of the first user.

* * * * *